United States Patent [19]
Liu et al.

[11] Patent Number: 5,756,516
[45] Date of Patent: May 26, 1998

[54] 1,2,3,4-TETRAHYDROISOQUINOLINE DERIVATIVES AND PHARMACEUTICAL COMPOSITION THEREOF

[75] Inventors: Lee-Tai Liu; Mei-Shey Lin; Ya-Chuan Lin; Su-Chen Yen; Hsiao-Jen Chen; Hsiang-Ling Huang; Chia-Lin Jeff Wang, all of Taipei, Taiwan

[73] Assignee: Development Center for Biotechnology, Taipei, Taiwan

[21] Appl. No.: 771,281

[22] Filed: Dec. 20, 1996

[30] Foreign Application Priority Data

Apr. 24, 1996 [CN] China .................. 85104900

[51] Int. Cl.⁶ .................. C07D 401/00; C07D 217/18; C07D 217/00; A01N 43/42
[52] U.S. Cl. .................. 514/307; 546/148; 546/149; 546/150
[58] Field of Search .................. 546/148, 149, 546/150; 514/307

[56] References Cited

U.S. PATENT DOCUMENTS

| 3,282,944 | 11/1966 | Walker et al. | 260/287 |
| 4,404,216 | 9/1983 | Richardson | 424/269 |

FOREIGN PATENT DOCUMENTS

| 0232989 | 8/1987 | European Pat. Off. |
| 0330360 | 8/1989 | European Pat. Off. |
| 4313118-A1 | 10/1994 | Germany |

OTHER PUBLICATIONS

"Chapter 2: Ergosterol Biosynthesis Inhibitors" in Scrip's *Antifungal Report—A review of progress in the development of new antifungals* (PJB Publications Ltd., BS 460) Sep. 1992, pp. 13–49.

*Primary Examiner*—John M. Ford
*Assistant Examiner*—Tamthom T. Ngo
*Attorney, Agent, or Firm*—McDonnell Boehnen Hulbert & Berghoff

[57] ABSTRACT

The invention relates to compounds of formula (I)

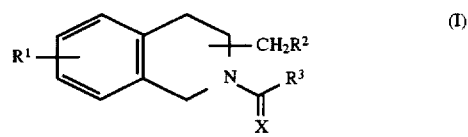

wherein $R^1$ is an optional substituent any position of phenyl ring and is selected from halogen, $-NO_2$, $-NH_2$, $-OH$ and $-O-CR_{1-6}$alkyl;

$-CH_2R^2$ is a substituent at 1- or 3- position of 1,2,3,4-tetrahydroisoquinoline, wherein $R^2$ is an azole group such as imidazole or triazole; and $R^3$ is phenyl optionally substituted with one or more halogen, and pharmaceutical salts thereof.

The compounds of formula (I) and salts thereof are useful as antifungal agents.

The invention also relates to the antifungal pharmaceutical compositions containing the compounds of formula (I), the methods of treating fungal infections using the compounds of formula (I) and the process for preparing the compounds of formula (I).

11 Claims, No Drawings

1,2,3,4-TETRAHYDROISOQUINOLINE DERIVATIVES AND PHARMACEUTICAL COMPOSITION THEREOF

TECHNICAL FIELD

The invention relates to 1,2,3,4-tetrahydroisoquinoline derivatives having a methyl substituted with a nitrogen-containing heterocyclic ring, antifungal pharmaceutical compositions containing the same, a method of treating fungal infections using the same and a process for preparing the same.

BACKGROUND OF THE INVENTION

An increase in the incidence of primary and opportunistic fungal infections has been observed in the medical community. There is a pressing need for accelerated development of new and more effective, as well as less toxic antifungal agents, especially for treating systemic infections.

Amphotericin B, a polyene macrolide, despite its toxicity, remains the most used of the systemic antifungal drugs. Recent work has focused on the development of triazoles as antifungal agents. The triazoles affect fungal membrane functions by inhibiting the action of lanosterol 14a-demethylase, a cytochrome P-450 enzyme. Fluconazol, as described in U.S. Pat. No. 4,404,216, is the current leading triazole drug in use, and has a high degree of specificity for the fungal enzyme.

However, increasing cases of resistance to fluconazole make it necessary to develop a new generation of antifungal agents.

SUMMARY OF THE INVENTION

One object of the invention is to provide novel antifungal compounds which are 1,2,3,4-tetrahydroisoquinoline derivatives having a methyl substituted with a nitrogen-containing heterocyclic ring.

Another object of the invention is to provide antifungal pharmaceutical compositions comprising novel 1,2,3,4-tetrahydroisoquinoline derivatives having a methyl substituted ring with a nitrogen-containing heterocyclic ring in a suitable pharmaceutical carrier.

Still another object of the invention is to provide a method of preventing or treating fungal infections in an individual by administrating novel 1,2,3,4-tetrahydroisoquinoline derivatives having a methyl substituted with a nitrogen-containing heterocyclic ring.

Further object of the invention is to provide methods for the preparation of novel 1,2,3,4-tetrahydroisoquinoline derivatives having a methyl substituted with a nitrogen-containing heterocyclic ring.

DETAILED DESCRIPTION OF THE INVENTION

The novel 1,2,3,4-tetrahydroisoquinoline derivatives, having a methyl substituted with a nitrogen-containing heterocyclic ring, of the subject invention are compounds of formula (I)

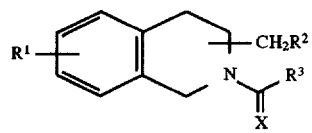

wherein $R^1$ is an optional substituent at any position of a phenyl ring and is selected from halogen, —$NO_2$, —$NH_2$, —OH and —O—$C_{1-6}$alkyl;

—$CH_2R^2$ is a substituent at the 1- or 3- position of 1,2,3,4-tetrahydroisoquinoline, wherein $R^2$ is a nitrogen-containing heterocyclic ring;

$R^3$ is phenyl optionally substituted with one or more halogen;

X is (H, H) or O;

and the pharmaceutical salts thereof.

The term "halogen" used herein refers to fluorine, chlorine, iodine and the like.

The term "alkyl" used herein refers to straight or branched alkyl groups having 1 to 6 carbon atoms, including methyl, ethyl, propyl, isopropyl, butyl, isobutyl, 1-methylpropyl, tert-butyl, pentyl, isopentyl, neopentyl and the like.

The term "nitrogen-containing heterocyclic ring" used herein refers to mono- or multi-cyclic structures containing one or more than one nitrogen atoms, including benzoheterocyclic rings such as pyrrole, imidazole, pyrazole, pyridine, pyrazine, quinoline, isoquinoline, carbazole, triazole, benzimidazole and the like.

The examples of specific compounds of formula (I) include, but are not limited to, the following:

2-Phenylmethyl-1-(1H-1,2,4-triazole-1-yl)methyl-1,2,3,4-tetrahydroisoquinoline (7a);

2-(4-Chlorophenyl)methyl-1-(1H-1,2,4-triazole-1-yl)methyl-1,2,3,4-tetrahydroisoquinoline (7b);

2-(4-Fluorophenyl)methyl-1-(1H-1,2,4-triazole-1-yl)methyl-1,2,3,4-tetrahydroisoquinoline (7c);

2-(2,4-Dichlorophenyl)methyl-1-(1H-1,2,4-triazole-1-yl)methyl-1,2,3,4-tetrahydroisoquinoline (7d);

2-(2,4-Difluorophenyl)methyl-1-(1H-1,2,4-triazole-1-yl)methyl-1,2,3,4-tetrahydroisoquinoline (7e);

(S)-2-Phenylmethyl-3-(1H-1,2,4-triazole-1-yl)methyl-1,2,3,4-tetrahydroisoquinoline (8a);

(S)-2-(4-Chlorophenyl)methyl-3-(1H-1,2,4-triazole-1-yl)methyl-1,2,3,4-tetrahydroisquinoline (8b);

(S)-2-(4-Fluorophenyl)methyl-3-(1H-1,2,4-triazole-1-yl)methyl-1,2,3,4-tetrahydroisoquinoline (8c);

(S)-2-(2,4-Dichlorophenyl)methyl-3-(1H-1,2,4-triazole-1-yl)methyl-1,2,3,4-tetrahydroisoquinoline (8d);

(S)-2-(2,4-Difluorophenyl)methyl-3-(1H-1,2,4-triazole-1-yl)methyl-1,2,3,4-tetrahydroisoquinoline (8e);

2-Phenylmethyl-1-(1H-1,3-imidazole-1-yl)methyl-1,2,3,4-tetrahydroisoquinoline (9a);

2-(4-Chlorophenyl)methyl-1-(1H-1,3-imidazole-1-yl)methyl-1,2,3,4-tetrahydroisoquinoline (9b);

2-(4-Fluorophenyl)methyl-1-(1H-1,3-imidazole-1-yl)methyl-1,2,3,4-tetrahydroisoquinoline (9c);

2-(2,4-Dichlorophenyl)methyl-1-(1H-1,3-imidazole-1-yl)methyl-1,2,3,4-tetrahydroisoquinoline (9d);

2-(2,4-Difluorophenyl)methyl-1-(1H-1,3-imidazole-1-yl)methyl-1,2,3,4-tetrahydro-isoquinoline (9e);

(S)-2-Phenylmethyl-3-(1H-1,3-imidazole-1-yl)methyl-1,2,3,4-tetrahydroisoquinoline (10a);

(S)-2-(4-Chlorophenyl)methyl-3-(1H-1,3-imidazole-1-yl)methyl-1,2,3,4-tetrahydroisoquinoline (10b);

(S)-2-(4-Fluorophenyl)methyl-3-(1H-1,3-imidazole-1-yl)methyl-1,2,3,4-tetrahydroisoquinoline (10c);

(S)-2-(2,4-Dichlorophenyl)methyl-3-(1H-1,3-imidazole-1-yl)methyl-1,2,3,4-tetrahydroisoquinoline (10d);

(S)-2-(2,4-Difluorophenyl)methyl-3-(1H-1,3-imidazole-1-yl)methyl-1,2,3,4-tetrahydro-isoquinoline (10e);

2-Phenylmethyl-1-(1H-1,3-benzimidazole-1-yl)methyl-1,2,3,4-tetrahydroisoquinoline (11a);

2-(4-Chlorophenyl)methyl-1-(1H-1,3-benzimidazole-1-yl)methyl-1,2,3,4-tetrahydroisoquinoline (11b);

2-(4-Fluorophenyl)methyl-1-(1H-1,3-benzimidazole-1-yl)methyl-1,2,3,4-tetrahydro-isoquinoline (11c);

2-(2,4-Dichlorophenyl)methyl-1-(1H-1,3-benzimidazole-1-yl)methyl-1,2,3,4-tetrahydro-isoquinoline (11d);

2-(2,4-Difluorophenyl)methyl-1-(1H-1,3-benzimidazole-1-yl)methyl-1,2,3,4-tetrahydro-isoquinoline (11e);

(S)-2-Phenylmethyl-3-(1H-1,3-benzimidazole-1-yl)methyl-1,2,3,4-tetrahydroisoquinoline (12a);

(S)-2-(4-Chlorophenyl)methyl-3-(1H-1,3-benzimidazole-1-yl)methyl-1,2,3,4-tetrahydroisoquinoline (12b);

(S)-2-(4-Fluorophenyl)methyl-3-(1H-1,3-benzimidazole-1-yl)methyl-1,2,3,4-tetrahydro-isoquinoline (12c);

(S)-2-(2,4-Dichlorophenyl)methyl-3-(1H-1,3-benzimidazole-1-yl)methyl-1,2,3,4-tetrahydroisoquinoline (12d);

(S)-2-(2,4-Difluorophenyl)methyl-3-(1H-1,3-benzimidazole-1-yl)methyl-1,2,3,4-tetrahydroisoquinoline (12e);

2-Phenylcarbonyl-1-(1H-1,2,4-triazole-1-yl)methyl-1,2,3,4-tetrahydroisoquinoline (13a);

2-(4-Chlorophenyl)carbonyl-1-(1H-1,2,4-triazole-1-yl)methyl-1,2,3,4-tetrahydroisoquinoline (13b);

2-(4-Fluorophenyl)carbonyl-1-(1H-1,2,4-triazole-1-yl)methyl-1,2,3,4-tetrahydroisoquinoline (13c);

2-(2,4-Dichlorophenyl)carbonyl-1-(1H-1,2,4-triazole-1-yl)methyl-1,2,3,4-tetrahydroisoquinoline (13d);

2-(2,4-Difluorophenyl)carbonyl-1-(1H-1,2,4-triazole-1-yl)methyl-1,2,3,4-tetrahydroisoquinoline (13e);

(S)-2-Phenylcarbonyl-3-(1H-1,2,4-triazole-1-yl)methyl-1,2,3,4-tetrahydroisoquinoline (14a);

(S)-2-(4-Chlorophenyl)carbonyl-3-(1H-1,2,4-triazole-1-yl)methyl-1,2,3,4-tetrahydroisoquinoline (14b);

(S)-2-(4-Fluorophenyl)carbonyl-3-(1H-1,2,4-triazole-1-yl)methyl-1,2,3,4-tetrahydroisoquinoline (14c);

(S)-2-(2,4-Dichlorophenyl)carbonyl-3-(1H-1,2,4-triazole-1-yl)methyl-1,2,3,4-tetrahydroisoquinoline (14d);

(S)-2-(2,4-Difluorophenyl)carbonyl-3-(1H-1,2,4-triazole-1-yl)methyl-1,2,3,4-tetrahydroisoquinoline (14e);

2-Phenylcarbonyl-1-(1H-1,3-imidazole-1-yl)methyl-1,2,3,4-tetrahydroisoquinoline (15a);

2-(4-Chlorophenyl)carbonyl-1-(1H-1,3-imidazole-1-yl)methyl-1,2,3,4-tetrahydroisoquinoline (15b);

2-(4-Fluorophenyl)carbonyl-1-(1H-1,3-imidazole-1-yl)methyl-1,2,3,4-tetrahydroisoquinoline (15c);

2-(2,4-Dichlorophenyl)carbonyl-1-(1H-1,3-imidazole-1-yl)methyl-1,2,3,4-tetrahydroisoquinoline (15d);

2-(2,4-Difluorophenyl)carbonyl-1-1-(1H-1,3-imidazole-1-yl)methyl-1,2,3,4-tetrahydroisoquinoline (15e);

(S)-2-Phenylcarbonyl-3-(1H-1,3-imidazole-1-yl)methyl-1,2,3,4-tetrahydroisoquinoline (16a);

(S)-2-(4-Chlorophenyl)carbonyl-3-(1H-1,3-imidazole-1-yl)methyl-1,2,3,4-tetrahydroisoquinoline (16b);

(S)-2-(4-Fluorophenyl)carbonyl-3-(1H-1,3-imidazole-1-yl)methyl-1,2,3,4-tetrahydroisoquinoline (16c);

(S)-2-(2,4-Dichlorophenyl)carbonyl-3-(1H-1,3-imidazole-1-yl)methyl-1,2,3,4-tetrahydroisoquinoline (16d);

(S)-2-(2,4-Difluorophenyl)carbonyl-3-(1H-1,3-imidazole-1-yl)methyl-1,2,3,4-tetrahydro-isoquinoline (16e);

2-Phenylcarbonyl-1-(1H-1,3-benzimidazole-1-yl)methyl-1,2,3,4-tetrahydroisoquinoline (17a);

2-(4-Chlorophenyl)carbonyl-1-(1H-1,3-benzimidazole-1-yl)methyl-1,2,3,4-tetrahydroisoquinoline (17b);

2-(4-Fluorophenyl)carbonyl-1-(1H-1,3-benzimidazole-1-yl)methyl-1,2,3,4-tetrahydroisoquinoline (17c);

2-(2,4-Dichlorophenyl)carbonyl-1-(1H-1,3-benzimidazole-1-yl)methyl-1,2,3,4-tetrahydro-isoquinoline (17d);

2-(2,4-Difluorophenyl)carbonyl-1-(1H-1,3-benzimidazole-1-yl)methyl-1,2,3,4-tetrahydro-isoquinoline (17e);

(S)-2-Phenylcarbonyl-3-(1H-1,3-benzimidazole-1-yl)methyl-1,2,3,4-tetrahydroisoquinoline (18a);

(S)-2-(4-Chlorophenyl)carbonyl-3-(1H-1,3-benzimidazole-1-yl)methyl-1,2,3,4-tetrahydroisoquinoline (18b);

(S)-2-(4-Fluorophenyl)carbonyl-3-(1H-1,3-benzimidazole-1-yl)methyl-1,2,3,4-tetrahydro-isoquinoline (18c);

(S)-2-(2,4-Dichlorophenyl)carbonyl-3-(1H-1,3-benzimidazole-1-yl)methyl-1,2,3,4-tetrahydroisoquinoline (18d); and (S)-2-(2,4-Difluorophenyl)carbonyl-3-(1H-1,3-benzimidazole-1-yl)methyl-1,2,3,4-tetrahydroisoquinoline (18e).

The preferred compounds of formula (I) include the following:

2-Phenylmethyl-1-(1H-1,2,4-triazole-1-yl)methyl-1,2,3,4-tetrahydroisoquinoline (7a);

2-(4-Chlorophenyl)methyl-1-(1H-1,2,4-triazole-1-yl)methyl-1,2,3,4-tetrahydroisoquinoline (7b);

2-(4-Fluorophenyl)methyl-1-(1H-1,2,4-triazole-1-yl)methyl-1,2,3,4-tetrahydroisoquinoline (7c);

2-(2,4-Dichlorophenyl)methyl-1-(1H-1,2,4-triazole-1-yl)methyl-1,2,3,4-tetrahydroisoquinoline (7d);

2-(2,4-Difluorophenyl)methyl-1-(1H-1,2,4-triazole-1-yl)methyl-1,2,3,4-tetrahydroisoquinoline (7e);

(S)-2-Phenylmethyl-3-(1H-1,2,4-triazole-1-yl)methyl-1,2,3,4-tetrahydroisoquinoline (8a);

(S)-2-(4-Chlorophenyl)methyl-3-(1H-1,2,4-triazole-1-yl)methyl-1,2,3,4-tetrahydroisoquinoline (8b);

(S)-2-(4-Fluorophenyl)methyl-3-(1H-1,2,4-triazole-1-yl)methyl-1,2,3,4-tetrahydroisoquinoline (8c);

(S)-2-(2,4-Dichlorophenyl)methyl-3-(1H-1,2,4-triazole-1-yl)methyl-1,2,3,4-tetrahydroisoquinoline (8d);

(S)-2-(2,4-Difluorophenyl)methyl-3-(1H-1,2,4-triazole-1-yl)methyl-1,2,3,4-tetrahydroisoquinoline (8e);

2-Phenylmethyl-1-(1H-1,3-imidazole-1-yl)methyl-1,2,3,4-tetrahydroisoquinoline (9a);

2-(4-Chlorophenyl)methyl-1-(1H-1,3-imidazole-1-yl)methyl-1,2,3,4-tetrahydroisoquinoline (9b);

2-(4-Fluorophenyl)methyl-1-(1H-1,3-imidazole-1-yl)methyl-1,2,3,4-tetrahydroisoquinoline (9c);

2-(2,4-Dichlorophenyl)methyl-1-(1H-1,3-imidazole-1-yl)methyl-1,2,3,4-tetrahydroisoquinoline (9d);

2-(2,4-Difluorophenyl)methyl-1-(1H-1,3-imidazole-1-yl)methyl-1,2,3,4-tetrahydro-isoquinoline (9e);

(S)-2-Phenylmethyl-3-(1H-1,3-imidazole-1-yl)methyl-1,2,3,4-tetrahydroisoquinoline (10a);

(S)-2-(4-Chlorophenyl)methyl-3-(1H-1,3-imidazole-1-yl)methyl-1,2,3,4-tetrahydroisoquinoline (10b);

(S)-2-(4-Fluorophenyl)methyl-3-(1H-1,3-imidazole-1-yl)methyl-1,2,3,4-tetrahydroisoquinoline (10c);

(S)-2-(2,4-Dichlorophenyl)methyl-3-(1H-1,3-imidazole-1-yl)methyl-1,2,3,4-tetrahydroisoquinoline (10d);

(S)-2-(2,4-Difluorophenyl)methyl-3-(1H-1,3-imidazole-1-yl)methyl-1,2,3,4-tetrahydro-isoquinoline (10e);

2-Phenylmethyl-1-(1H-1,3-benzimidazole-1-yl)methyl-1,2,3,4-tetrahydroisoquinoline (11a);

2-(4-Chlorophenyl)methyl-1-(1H-1,3-benzimidazole-1-yl)methyl-1,2,3,4-tetrahydroisoquinoline (11b);

2-(4-Fluorophenyl)methyl-1-(1H-1,3-benzimidazole-1-yl)methyl-1,2,3,4-tetrahydro-isoquinoline (11c);

2-(2,4-Dichlorophenyl)methyl-1-(1H-1,3-benzimidazole-1-yl)methyl-1,2,3,4-tetrahydro-isoquinoline (11d); and 2-(2,4-Difluorophenyl)methyl-1-(1H-1,3-benzimidazole-1-yl)methyl-1,2,3,4-tetrahydro-isoquinoline (11e).

The more preferred compounds of formula (I) include the following:

2-(4-Chlorophenyl)methyl-1-(1H-1,2,4-triazole-1-yl)
methyl-1,2,3,4-tetrahydroisoquinoline (7b);
2-(4-Chlorophenyl)methyl-1-(1H-1,3-imidazole-1-yl)
methyl-1,2,3,4-tetrahydroisoquinoline (9b); and
2-(2,4-Dichlorophenyl)methyl-1-(1H-1,3-imidazole-1-yl)
methyl-1,2,3,4-tetrahydroisoquinoline (9d).

The compounds of formula (I) may be prepared from aminoalcohol 1 or 2 according to Schemes 1 to 4.

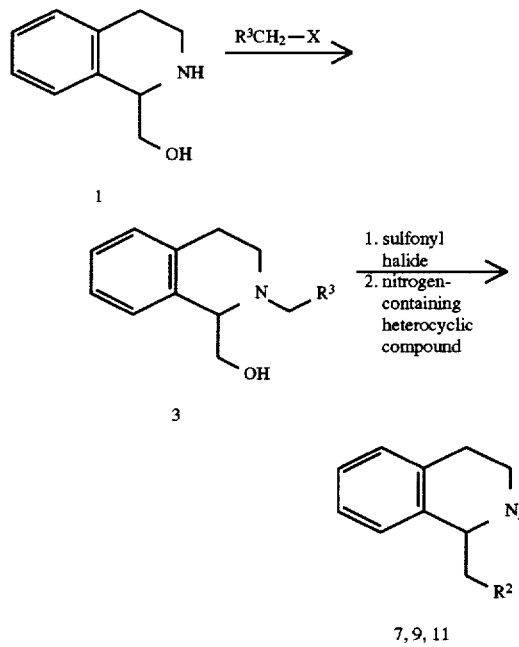

In Scheme 1, aminoalcohol 1 is reacted with the compound of formula $R^3CH_2$—X in the presence of a suitable base in a suitable organic solvent to obtain a tertiary amine 3. In the formula $R^3CH_2$—X, $R^3$ is defined as hereinbefore and X is halogen such as fluorine, chlorine and bromine. Therefore the compound of formula $R^3CH_2$—X may be benzyl chloride or benzyl bromide, and benzyl bromide is preferred.

The suitable base may be any organic or inorganic base commonly used in the art such as sodium carbonate and potassium carbonate. The suitable organic solvent can be any organic solvent commonly used in the art. Dimethylformamide (DMF) is preferred. In general, the above reaction is performed at a temperature between 10° to 50° C., preferably about 20° C., for about 2 hours.

The amino alcohol 3 may be separated and purified by conventional methods such as extraction and chromatography. The hydroxy group of the amino alcohol 3 is further converted to a sulfonate. For example, the amino alcohol 3 may be reacted with a methylsulfonyl halide in the presence of an organic base to convert the hydroxy group to $OSO_2CH_3$. Suitable sulfonyl halides include methylsulfonyl chloride, benzylsulfonyl chloride, toluenesulfonyl chloride and the like, and methylsulfonyl chloride is preferred.

In the reaction converting the hydroxy group to the methylsulfonate, any organic base commonly used in the art is useful, and triethylamine is preferred. Similarly, any organic solvents commonly used in the art are useful in the conversion reaction. For example, halohydrocarbons such as dichloromethane may be used in the reaction. The conversion reaction is preferably performed at a lowered temperature between 0° C. to room temperature generally for about 20 minutes to about 2 hours.

The intermediates produced in the conversion reaction are further reacted with nitrogen-containing heterocyclic compounds, for example, in the presence of a base in a suitable organic solvent to produce compounds 7, 9 and 11.

The examples of nitrogen-containing heterocyclic compounds are pyrrole, imidazole, pyrazole, pyridine, pyrazine, quinoline, isoquinoline, carbazole, triazole, benzimidazole and the like, and triazole, imidazole as well as benzimidazole are preferred.

The base may be any base commonly used in the art such as sodium carbonate and potassium carbonate. The suitable organic solvent can be any organic solvents commonly used in the art such as dimethylformamide. The reaction with nitrogen-containing heterocyclic compounds is preferably performed at an elevated temperature. An elevated temperature refers to a temperature generally between 30° C.–70° C., and 50° C.–60° C. is most preferred. The reaction is generally completed in about 12 to 20 hours. The products 7, 9 and 11 may be separated and purified by conventional methods such as extraction and chromatography.

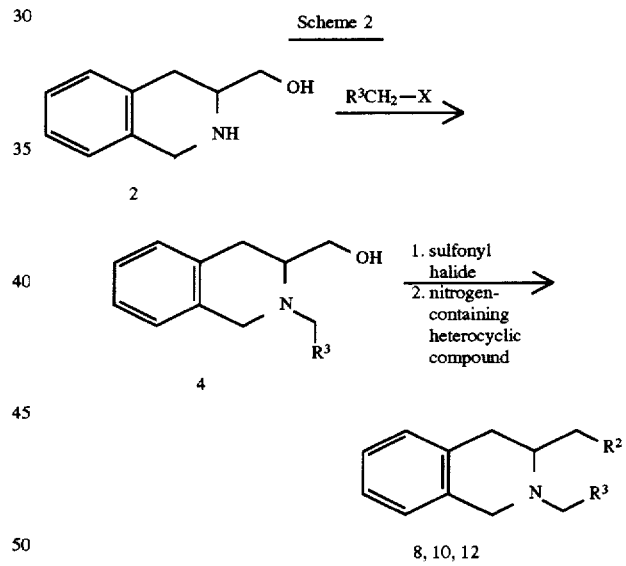

In Scheme 2, aminoalcohol 2 is reacted as the starting material according to the conditions and protocols described in Scheme 1 to produce compounds 8, 10 and 12.

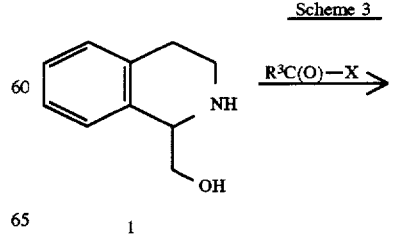

Scheme 3 -continued

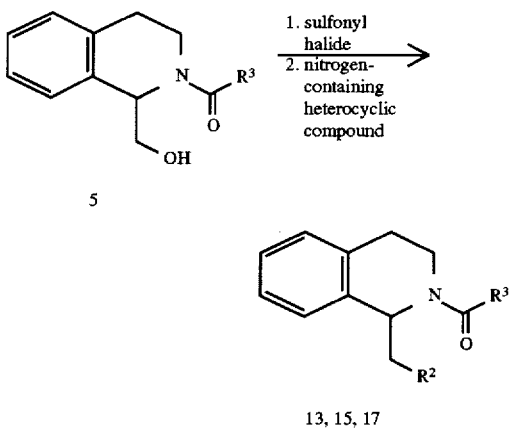

In Scheme 3, aminoalcohol 1 and the compound of formula $R^3C(O)$—X (wherein $R^3$ and X are defined as hereinbefore) are reacted in a suitable organic solvent to form amide 5. Any suitable organic solvents such as halo-hydrocarbons are useful in the scheme. Dichloromethane is preferred. The reaction is generally performed at a lowered temperature, for example, around 0° C. Then, the hydroxy group of amide 5 is converted to compounds 13, 15 and 17 in a manner 30 similar to that described in Scheme 1.

Scheme 4

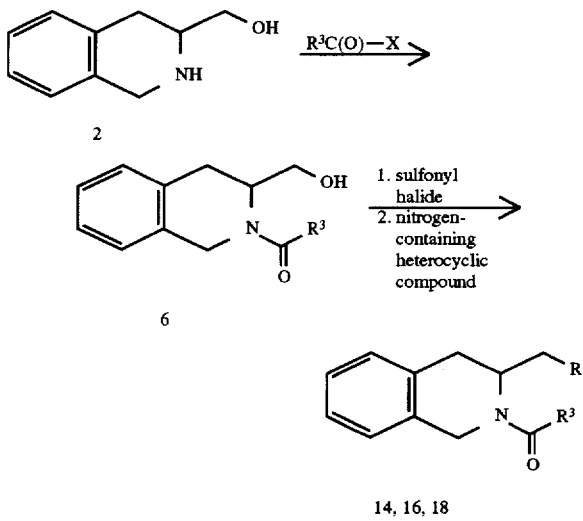

In Scheme 4, aminoalcohol 2 is reacted as the starting material according to the conditions and protocols described in Scheme 3 to produce compounds 14, 16 and 18.

The pharmaceutically acceptable salts of the compounds of formula (I) of the subject invention are preferably in the form of an acid addition salt including those non-toxic salts derived from inorganic or organic acids. Pharmaceutically acceptable salts include, but are not limited to, salts with inorganic acids such as hydrochloride, hydrobromide, sulfate and the like. The salts may be prepared by conventional methods, for example, mixing the solution containing the free base of the compounds of the subject invention with a solution containing the desired acid in an equimolar ratio, followed by recovering the desired salts by filtration if the salt obtained is insoluble or by evaporation of the solvents in the system according to the standard techniques.

The compounds of the subject invention and the pharmaceutically acceptable salts thereof are very effective antifungal agents and are useful in the treatment and prevention of fungal infections in human and animals. For example, the compounds are useful in the treatment and prevention of topical infections with molds or yeasts including Aspergillus flavus, Aspergillus fumigatus, Fusarium oxysporum, Trichophyton mentagrophytes, Cryptococcus neoformans, Candida kefyr and Candida kefyr.

Formulations of the present invention for medical use comprise a compound of formula (I) as an active ingredient together with a pharmaceutically acceptable carrier thereof and optionally other therapeutically active ingredients. The present invention, therefor, further provides an antifungal pharmaceutical composition comprising a compound of formula (I) together with a pharmaceutically acceptable carrier thereof. The present invention also provides a method of preventing or treating antifungal infections in an individual which comprises administrating to such individual an antifungal effective amount of the compound of formula (I) in combination with a pharmaceutically acceptable carrier.

The amount of compound of formula (I) required to be effective as antifungal agent varies with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective antifungal dose is in the range of about 0.01 to about 5.0 mg/kg body weight per day. The total daily dose may be given as a single dose, multiple doses, e.g., two to six times per day, or by intravenous infusion for a selected duration.

The formulations include those suitable for oral, rectal, topical or parenteral (including subcutaneous, intramuscular and intravenous) administration.

Formulations of the present invention suitable for oral administration may be presented as discrete units such as capsules, cachets, tablets or lozenges, each containing a predetermined amount the active compound; as a powder or granules; or as a suspension or solution in an aqueous liquid or non-aqueous liquid, e.g., a syrup, an elixir, an emulsion or a draught.

Formulations for rectal administration may be presented as a suppository with a conventional carrier, e.g., cocoa butter, for a suppository base.

Formulations suitable for parental administration conveniently comprise a sterile aqueous preparation of the active compound which is preferably isotonic with the blood of the recipient. Such formulations suitably comprise a solution or suspension of a pharmaceutically acceptable acid addition salt of a compound of the formula (I) that is isotonic with the blood of the recipient.

Topical formulations may include ointments, creams, gels, and lotions which may be prepared by conventional methods known in the art of pharmacy.

In addition, to the aforementioned ingredients, the compositions of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

The following examples illustrate aspects of this invention but should not be construed as limitations.

EXAMPLES

Example 1
Preparation of compounds 7 and 8

(1) 2-Phenylmethyl-1-(1H-1,2,4-triazole-1-yl)methyl-1,2,3,4-tetrahydroisoquinoline (7a)

Take compound 7a as an example to describe the general procedures for preparing compounds 7–12. To a DMF suspension of compound 1 (or 2) (1 equivalent) and $Na_2CO_3$ (2 equivalents) in a round-bottom flask was added benzyl bromide or chloride (1.2 equivalents). After stirring at room temperature for 2 hours, the mixture was poured into water and then extracted with EtOAc. The organic layer was dried over $MgSO_4$. After removal of solvent, the crude product was purified by column chromatography to afford compound 3 as a thick yellow liquid (about 50–75% yield).

To a $CH_2Cl_2$ solution of compound 3 (1 equivalent) and triethylamine (2 equivalents) in an ice bath was added methanesulfonyl chloride (1.2 equivalents). After stirring at 0° C. for 30 min and at room temperature for 1 hour, the mixture was concentrated and filtered. The organic solution was concentrated to dryness and dissolved in a suitable amount of DMF. To this pale yellow mass was added 2 equivalents of $Na_2CO_3$ and 1.5 equivalents of 1,2,4-triazole. The suspension was heated in an oil bath at 50°–60° C. for 16 hours. After incubation, the DMF suspension is poured into water and extracted with EtOAc. The organic layer was then dried over $MgSO_4$. The crude product was purified by column chromatography to provide the compound 7a as a thick yellow liquid (about 35–55% yield).

Thick liquid. 1H NMR (200 MHz, $CDCl_3$) d 7.99 (s, 1H, triazole CH), 7.87 (s, 1H, triazole CH), 7.29–6.99 (m, 9H, Ar H), 4.37–4.32 (m, 2H, $CH_2N$), 4.05 (dd, J=4.8, 8.3 Hz, 1H, ArCHN), 3.74 (d, J=13.2 Hz, 1H, NCHHPh), 3.62 (d, J=13.2 Hz, 1H, NCHHPh), 3.30–2.30 (m, 4 H, $ArCH_2CH_2N$). HRMS (EI) Calcd for $C_{19}H_{20}N_4$ 304.1688. Found 304.1684.

(2) 2-(4-Chlorophenyl)methyl-1-(1H-1,2,4-triazole-1-yl)methyl-1,2,3,4-tetrahydroisoquinoline (7b)

Thick liquid. 1H NMR (200 MHz, $CDCl_3$) d 7.98 (s, 1H, triazole CH), 7.89 (s, 1H, triazole CH), 7.37–6.90 (m, 8H, Ar H), 4.37–4.32 (m, 2H, $CH_2N$), 4.03 (dd, J=8.2, 5.4, Hz, 1H, ArCHN), 3.71 (d, J=13.3 Hz, 1H, NCHHAr), 3.58 (d, J=13.3 Hz, 1H, NCHHAr), 3.40–2.40 (m, 4H, $ArCH_2CH_2N$). HRMS (EI) Calcd for $C_{19}H_{19}N_4Cl$ 338.1298. Found 338.1290. Anal. Calcd for $C_{18}H_{19}N_4Cl$: C, 67.35; H, 5.65; N 16.53. Found: C, 67.75; H, 5.75; N, 16.31.

(3) 2-(4-Fluorophenyl)methyl-1-(1H-1,2,4-triazole-1-yl)methyl-1,2,3,4-tetrahydroisoquinoline (7c)

Thick liquid. 1H NMR (200 MHz, $CDCl_3$) d 7.99 (s, 1H, triazole CH), 7.89 (s, 1H, triazole CH), 7.29–6.89 (m, 8H, Ar H), 4.36–4.32 (m, 2H, $CH_2N$), 4.03 (dd,J=8.3, 5.5 Hz, 1H, ArCHN), 3.71 (d, J=13.1 Hz, 1H, NCHHAr), 3.58 (d, J=13.1 Hz, 1H, NCHHAr), 3.40–2.40 (m, 4H, $ArCH_2CH_2N$). HRMS (EI) Calcd for $C_{19}H_{19}N_4F$ 322.1594. Found 322.1565.

(4) 2-(2,4-Dichlorophenyl)methyl-1-(1H-1,2,4-triazole-1-yl)methyl-1,2,3,4-tetrahydro-isoquinoline (7d)

Thick liquid. 1H NMR (200 MHz, $CDCl_3$) d 7.93 (s, 1H, triazole CH), 7.81 (s, 1H, triazole CH), 7.28–6.87 (m, 7H, Ar H), 4.34–4.30 (m, 2H, $CH_2N$), 4.08–4.02 (m;, 1H, ArCHN), 3.82 (d, J=13.4 Hz, 1H, NCHHAr), 3.64 (d, J=13.4 Hz, 1H, NCHHAr), 3.40–2.30 (m, 4H, $ArCH_2CH_2N$). HRMS (EI) Calcd for $C_{19}H_{18}N_4C_{12}$—$H_2$ 370.0752. Found 370.0732.

(5) 2-(2,4-Difluorophenyl)methyl-1-(1H-1,2,4-triazole-1-yl)methyl-1,2,3,4-tetrahydro-isoquinoline (7e)

Thick liquid. 1H NMR (200 MHz, $CDCl_3$) d 7.98 (s, 1H, triazole CH), 7.85 (s, 1H, triazole CH), 7.27–6.68 (m, 7H, Ar H), 4.35 (d, 2H,J=6.6 Hz,$CH_2N$), 4.06 (t, 1H, J=6.6 Hz, ArCHN), 3.77 (d, J=13.5 Hz, 1H, NCHHAr), 3.63 (d, J=13.5 Hz, 1H, NCHHAr), 3.40–2.30 (m, 4H, $ArCH_2CH_2N$). HRMS (EI) Calcd for $C_{19}H_{18}N_4F_2$—$H_2$ 338.1343. Found 338.1337.

(6) (S)-2-Phenylmethyl-3-(1H-1,2,4-triazole-1-yl)-methyl-1,2,3,4-tetrahydroisoquinoline (8a)

Thick liquid. 1H NMR (200 MHz, $CDCl_3$) d 8.15 (s, 1H, triazole CH), 8.02 (s, 1H, triazole CH), 7.36–7.00 (m, 9H, Ar H), 4.35 (dd, J=13.8, 7.0 Hz, 1H, CHHN), 4.5 (dd, J=13.8, 6.8 Hz, 1H, CHHN), 3.90–3.61 (m, 5H, $CH_2N(CH)CH_2Ph$), 3.04 (dd, J=16.2, 5.7 Hz, 1H, ArCHH), 2.53 (dd, J=16.2, 4.06 Hz, 1H, ArCHH). HRMS (EI) Calcd for $C_{19}H_{20}N_4$ 304.1688. Found 304.1695.

(7) (S)-2-(4-Chlorophenyl)methyl-3-(1H-1,2,4-triazole-1-yl)methyl-1,2,3,4-tetrahydro-isoquinoline (8b)

Thick liquid. 1H NMR (200 MHz, $CDCl_3$) d 8.03 (s, 1H, triazole CH), 7.97 (s, 1H, triazole CH), 7.30–7.00 (m, 8H, Ar H), 4.35 (dd, J=13.8, 7.2 Hz, 1H, CHHN), 4.5 (dd, J=13.8, 6.8 Hz, 1H, CHHN), 3.89–3.55(m, 5H, $CH_2N(CH)CH_2Ph$), 3.05 (dd, J=16.5, 5.8 Hz, 1H, ArCHH), 2.52 (dd, J=16.5, 4.15 Hz, 1H, ArCHH). HRMS (EI) Calcd for $C_{19}H_{19}N_4Cl$ 338.1298. Found 338.1299.

(8) (S)-2-(4-Fluorophenyl)methyl-3-(1H-1,2,4-triazole-1-yl)methyl-1,2,3,4-tetrahydro-isoquinoline (8c)

Thick liquid. 1H NMR (200 MHz, $CDCl_3$) d 8.04 (s, 1H, triazole CH), 7.97 (s, 1H, triazole CH), 7.33–6.95 (m, 8H, Ar H), 4.35 (dd,J=13.7, 7.1 Hz, 1H, CHHN), 4.5 (dd, J=13.7, 6.8 Hz, 1 H,CHHN), 3.88–3.56 (m, 5H, $CH_2N(CH)CH_2Ph$), 3.05 (dd, J=16.5, 5.5 Hz, 1H, ArCHH), 2.52 (dd, J=16.5, 4.1 Hz, 1H, ArCHH). HRMS (EI) Calcd for $C_{19}H_{19}N_4F$ 322.1594. Found 322.1588.

(9) (S)-2-(2,4-Dichlorophenyl)methyl-3-(1H-1,2,4-triazole-1-yl)methyl-1,2,3,4-tetrahydroisoquinoline (8d)

Thick liquid. 1H NMR (200 MHz, $CDCl_3$) d 8.00 (s, 1H, triazole CH), 7.95(s, 1H, triazole CH), 7.37–7.02 (m, 7H, Ar H), 4.38 (dd, J=13.7, 7.1 Hz, 1H, CHHN), 4.13 (dd, J=13.8, 6.9 Hz, 1H, CHHN), 3.95–3.65 (m, 5H, $CH_2N(CH)CH_2Ph$), 3.10 (dd, J=16.2, 5.7 Hz, 1H, ArCHH), 2.55 (dd, J=16.4, 4.04 Hz, 1H, ArCHH). HRMS (EI) Calcd for $C_{19}H_{18}N_4C_{12}$+H 373.0987. Found 373.0927.

(10) (S)-2-(2,4-Difluorophenyl)methyl-3-(1H-1,2,4-triazole-1-yl) methyl-1,2,3,4-tetrahydroisoquinoline (8e)

Thick liquid. 1H NMR (200 MHz, $CD_3Cl$) d 8.00 (s, 1H, triazole CH), 7.95 (s, 1H, triazole CH), 7.27–6.75 (m, 7H, Ar H), 4.36 (dd, J=13.8, 6.8 Hz, 2H,CHHN), 4.13 (dd, J=13.6, 6.9 Hz, 1H, CHHN), 3.90–3.60 (m, 5H, $CH_2N(CH)CH_2Ph$), 3.04 (dd, J=15.8, 5.8 Hz, 1H, ArCHH), 2.54 (dd, J=16.3, 4.3 Hz, 1H, ArCHH). HRMS (EI) Calcd for $C_{19}H_{18}N_4F_2$ 340.1499. Found 340.1493.

Example 2
Preparation of compounds 9–18

The general procedures for preparing compounds 9–12 were similar to those for preparing compound 7. 1,3-imidazole was used for preparing compounds 9 and 11 and 1,3-benzimidazole was used for preparing compounds 10 and 12.

(1) 2-Phenylmethyl-1-(1H-1,3-imidazole-1-yl)methyl-1,2,3,4-tetrahydroisoquinoline (9a)

Thick liquid. 1H NMR (200 MHz, $CDCl_3$) d 8.00 (s, 1H, imidazole H), 7.56–6.46 (m, 5H, Ar H and imidazole CH), 4.19 (dd, J=7.3, 14.2 Hz, 1H, CHHN), 4.06 (dd, J=4.4, 14.2 Hz, 1H, CHHN), 3.95–3.68 (m, 3H, $ArCHNCH_2Ph$), 3.30–2.30 (m, 4H, $ArCH_2CH_2N$). HRMS (EI) Calcd for $C_{20}H_{21}N_3$ 303.1735. Found 303.1737.

(2) 2-(4-Chlorophenyl)methyl-1-(1H-1,3-imidazole-1-yl) methyl-1,2,3,4-tetrahydroisoquinoline (9b)

Thick liquid. 1H NMR (500 MHz, $CDCl_3$) d 8.15–6.70 (m, 5H, Ar H and imidazole CH), 4.16 (dd, J=8.0, 14.3 Hz, 1H, CHHN), 4.05 (dd, J=4.5, 14.3 Hz, 1H, CHHN), 3.95–3.50 (m, 3H, ArCHNCH$_2$Ph), 3.50–2.35 (m, 4H, ArCH$_2$CH$_2$N). HRMS (EI) Calcd for C$_{20}$H$_{20}$N$_3$Cl 337.1346. Found 337.1339.

(3) 2-(4-Fluorophenyl)methyl-1-(1H-1,3-imidazole-1-yl) methyl-1,2,3,4-tetrahydroisoquinoline (9c)

Thick liquid. 1H NMR (500 MHz, CDCl$_3$)) d 7.50–6.60 (m, 5H, Ar H and imidazole CH), 4.18 (dd, J=8.0, 14.3 Hz, 1H, CHHN), 4.07 (dd, J=4.5, 14.3 Hz, 1H, CHHN), 3.86 (q, J=4.5 Hz, 1H, CHN), 3.85–3.60 (m, 2H, NCH$_2$Ph), 3.30–2.75 (m, 4H, ArCH$_2$CH$_2$N). HRMS (EI) Calcd for C$_{20}$H$_{20}$N$_3$F 321.1641. Found 321.1649.

(4) 2-(2,4-Dichlorophenyl)methyl-1-(1H-1,3-imidazole-1-yl)methyl-1,2,3,4-tetrahydro-isoquinoline (9d)

Thick liquid. 1H NMR (500 MHz, CDCl$_3$) d 7.36–6.97 (m, 10H, Ar H and imidazole CH), 6.70 (s, 1H, imidazole CH), 4.17 (dd, J=7.7, 14.4 Hz, 1H, CHHN), 4.09 (dd, J=4.4, 14.3 Hz, 1H, CHHN) 3.89 (m, 1H, CHN), 3.86 (d, 1H, NCHHPh), 3.78 (d, 1H, NCHHPh), 3.20–2.47 (m, 4H, ArCH$_2$CH$_2$N).

HRMS (EI) Calcd for C$_{20}$H$_{19}$N$_3$Cl$_2$ 371.0956. Found 371.0922.

(5) 2-(2,4-Difluorophenyl)methyl-1-(1H-1,3-imidazole-1-yl)methyl-1,2,3,4-tetrahydro-isoquinoline (9e)

Thick liquid. 1H NMR (500 MHz, CDCl$_3$) d 7.55–6.65 (m, 10H, Ar H and imidazole CH), 4.15–4.6 (m, 2H, CH$_2$N), 3.89 (m 1H, CHN), 3.78–3.71 (m, 2H, NCH$_2$Ph), 3.18–2.40 (m, 4H, ArCH$_2$CH$_2$N). HRMS (EI) Calcd for C$_{20}$H$_{19}$N$_3$F$_2$ 339.1547. Found 339.1548.

(6) 2-Phenylmethyl-1-(1H-1,3-benzimidazole-1-yl)-methyl-1,2,3,4-tetrahydroisoquinoline (11a)

Thick liquid. 1H NMR (200 MHz, CDCl$_3$) d 8.00 (s, 1H, imidazole H), 7.56–6.46 (m, 5H, Ar H and imidazole CH), 4.19 (dd, J=7.3, 14.2 Hz, 1H, CHHN), 4.06 (dd, J=4.4, 14.2 Hz, 1H, CHHN), 3.95–3.68 (m, 3H, ArCHNCH$_2$Ph), 3.30–2.30 (m, 4H, ArCH$_2$CH$_2$N). HRMS (EI) Calcd for C$_{24}$H$_{23}$N$_3$ 353.1892. Found 353.1896.

(7) 2-(4-Chlorophenyl)methyl-1-(1H-1,3-benzimidazole-1-yl)methyl-1,2,3,4-tetrahydro-isoquinoline (11b)

Thick liquid. 1H NMR (500 MHz, CDCl$_3$) d 8.15–6.70 (m, 5H, Ar H and imidazole CH), 4.16 (dd, J=8.0, 14.3 Hz, 1H, CHHN), 4.05 (dd, J=4.5, 14.3 Hz, 1H, CHHN), 3.95–3.50 (m, 3H, ArCHNCH$_2$Ph), 3.50–2.35 (m, 4H, ArCH$_2$CH$_2$N). HRMS (EI) Calcd for C$_{24}$H$_{22}$N$_3$Cl 387.1502. Found 387.1486.

(8) 2-(4-Fluorophenyl)methyl-1-(1H-1,3-benzimidazole-1-yl)methyl-1,2,3,4-tetrahydro-isoquinoline (11c)

Thick liquid. 1H NMR (500 MHz, CDCl$_3$) d 7.50–6.60 (m, 5H, Ar H and imidazole CH), 4.18 (dd, J=8.0, 14.3 Hz, 1H, CHHN), 4.07 (dd, J=4.5, 14.3 Hz, 1H, CHHN), 3.86 (q, J=4.5 Hz, 1H, CHN), 3.85–3.60 (m, 2H, NCH$_2$Ph), 3.30–2.75 (m, 4H, ArCH$_2$CH$_2$N). HRMS (EI) Calcd for C$_{24}$H$_{22}$N$_3$F 371.1798. Found 371.1782.

(9) 2-(2,4-Dichlorophenyl)methyl-1-(1H-1,3-benzimidazole-1-yl)methyl-1,2,3,4-tetrahydro-isoquinoline (11d)

Thick liquid. 1H NMR (500 MHz, CDCl$_3$) d 7.36–6.97 (m, 10H, Ar H and imidazole CH), 6.70 (s, 1H, imidazole CH), 4.17 (dd, J=7.7, 14.4 Hz, 1H, CHHN), 4.09 (dd, J=4.4, 14.3 Hz, 1H, CHHN), 3.89 (m, 1H, CHN), 3.86 (d, 1H, NCHHPh), 3.78 (d, 1H, NCHHPh), 3.20–2.47 (m, 4H, ArCH$_2$CH$_2$N).

HRMS (EI) Calcd for C$_{24}$H$_{21}$N$_3$Cl$_2$+H 422.1191. Found 422.1154.

(10) 2-(2,4-Difluorophenyl)methyl-1-(1H-1,3-benzimidazole-1-yl) methyl-1,2,3,4-tetrahydro-isoquinoline (11e)

Thick liquid. 1H NMR (500 MHz, CDCl$_3$) d 7.55–6.65 (m, 10H, Ar H and imidazole CH), 4.15–4.6 (m, 2H, CH$_2$N), 3.89 (m 1H, CHN), 3.78–3.71 (m, 2H, NCH$_2$Ph), 3.18–2.40 (m, 4H, ArCH$_2$CH$_2$N). HRMS (EI) Calcd for C$_{24}$H$_{21}$N$_3$F$_2$ 389.1704. Found 389.1674. Anal. Calcd for C$_{24}$H$_{21}$N$_3$F$_2$ C, 74.02; H, 5.44; N 10.79. Found: C, 73.97; H, 5.71; N, 10.49.

Compounds 13–18 may be prepared by reacting aminoalcohol 1 or 2 with various phenyl carbonyl halides according to Schemes 3 and 4 in a similar manner to produce amide 5 or 6, followed by reacting the amide 5 or 6 with a suitable nitrogen-containing heterocyclic compound to convert the hydroxy group.

Example 3
Preparation of antifungal pharmaceutical compositions

Pharmaceutical compositions can be prepared with the compounds prepared as described in Examples 1 and 2 as an active ingredient. The ingredients according to the following formulation are mixed and compressed into tabulates.

| | |
|---|---|
| Active ingredient (e.g. 7b) | 100 mg |
| Lactose | 150 mg |
| Cellulose | 150 mg |
| Magnesium stearate | 6 mg |

Example 4
Evaluation of antifungal activities of compounds (1) Macrobroth dilution-filamentous fungi (molds) as test strains A. Test strains:

*Aspergillus flavus* (CCRC 30006)

*Aspergillus fumigatus* (CCRC 30502)

*Fusarium oxysporum* (CCRC 32121)

*Trichophyton mentagrophytes* (CCRC 32066)

B. Medium: Sabouraud Agar Modified (Difco)

RPMI 1640 (Sigma): 10.4 g of RPMI 1640 was completely dissolved in 1 L of 0.165M MOSP buffer solution. The solution was adjusted to pH 7.5, sterilized by filtration and dispersed to aliquots for use.

C. The preparation of standard antifungal agents:

Two antifungal agents, Amphotericin B (Sigma) and Miconazole (Sigma), were weighed out and dissolved in DMSO (dimethyl sulfoxide, Sigma) to produce solutions having a concentration of 1 mg/ml for use.

D. Inocula:

(a) Some spores or hyphae were picked out from the seed stocks of each test strain in test tubes and inoculated to Sabouraud Agar. The inoculated agar was actively cultured at 30° C. for 48 hours and then a piece of hypha was taken from the edge of colonies with a sterile punch (with a diameter of 3.0 mm) for use as seed test strain.

(b) Suitable amount of each of the antifungal agents was diluted with RPMI medium to produce a solution having a concentration of 25 ug/ml followed by inoculation of a piece of hypha. The medium was cultured at 35° C. for 48 hours with agitation. The growth of fungi was observed and the test agents were primarily screened. The agents having antifungal activities were further diluted at $2^{-n}$ series and tested to determine Minimum Inhibitory Concentration (MIC).

E. The determination of Minimum Inhibitory Concentration:

The Minimum Inhibitory Concentration was determined as the lowest concentration of the antifungal agent which made hyphal growth in the test tube unobservable with the waked eye.

(2) Microbroth dilution: for use with yeast test strains

A. Test strains:

Cryptococcus neoformans (CCRC 20528)

Candida albicans (CCRC 21538)

Candida guilliermondii (CCRC 21500)

Candida krusei (CCRC 21321)

Candida tropicalis (CCRC 20521)

Candida kefyr (CCRC 20517)

B. Medium: Sabouraud Dextrose Agar (Difco), RPMI 1640-MOSP (pH 7.0)(Sigma). 1.04 g of RPMI 1640 (Sigma) was dissolved in 100 ml of distilled water followed by the addition of 3.45 g of MOSP (Sigma). After complete dissolution, the solution was adjusted with 10M NaOH to pH 7.0 and sterilized by filtration through membranes. The solution was stored at 4° C. until use.

C. The preparation of standard solutions of antifungal agents (as described in (1)C)

D. The preparation of inocula:

Test strains were inoculated in Sabouraud Dextrose Agar and actively cultured at 30° C. for 48 hours. Five single colonies were picked out and agitated in sterile water (0.85% NaCl) for 15 seconds to form yeast suspensions. The number of yeast was counted under microscope with hemocytometer and the yeast suspension was diluted to the required yeast concentration. Because of the slow growth rate, C. neoforman had an initial inoculation concentration of $1-3\times10^6$ CFU/ml and a final incoculation amount of $1-3\times10^4$ CFU. C. albicans had an initial inoculation concentration of $1-3\times10^4$ CFU/ml and a final incoculation amount of $1-3\times10^2$ CFU.

E. To a 96-well microtiter plate, medium (RPMI-MOPS, pH 7.0) was first added and then the antifungal agents were added according to the experimental design. The initial concentration of antifungal agent was 50 ug/ml and was diluted in $2^{-n}$ series to 50, 25, ... 0.2, 0.1 ug/ml before being added to the microtiter plate. The test strains were then added to the microtiter plate and cultured at 35° C. for 48 hours and the turbidity was observed with the waked eye to determine the growth of yeast. MIC value indicates the minimum dosage concentration for obtaining 50% growth inhibition.

(3) Results:

1. As shown in Table 1 and Table 3, among 10 triazole derivatives (7,8), only compound 7b has better antifungal activities. The Minimum Inhibition Concentration (MIC) values for Cryptococcus neoforma and Candida kefyr were respectively 6.25 and 0.39 ug/ml; The MIC values for Aspergillus spp. and Trichophyton mentagrophytes were respectively 0.25 and 4.25 ug/ml.

2. As shown in Table 2 and Table 4, from among 10 Imidazole compounds (9,11), 3 compounds, 9b, 9d and 11b, exhibited better inhibition effect against yeasts; compounds 9a, 9b, 9c, 9d and 9e exhibited significant inhibition effect against molds. Compounds 9b and 9d exhibited significant antifungal activities with broad-spectrum activity against both yeasts and molds. For compound 9b, the MIC values for yeasts Cryptococcus neoforma and Candida kefyr were 0.39 and 0.10 ug/ml respectively; the MIC values for molds Aspergillus spp. and Trichophyton mentagrophytes were 3.12, 0.19 and 0.19 ug/ml respectively. For compound 9d, the MIC values for yeasts Cryptococcus neoforma and Candida kefyr were 1.56 and 0.19 ug/ml respectively; the MIC values for molds Aspergillus spp. and Trichophyton mentagrophytes were 0.39, 0.78 and 6.25 ug/ml respectively.

3. The in vitro MIC value of compounds 7b, 9b and 9d are better than that of Fluconazole, which is a commercially available antifungal azole compound. The comparative results show that compounds 7b, 9b and 9d are effective novel antifungal agent.

TABLE I

The In vitro Susceptibility Testing of Triazole Antifungals agains yeasts

| CCRC# Strain | MIC (ug/ml) | | | | | |
|---|---|---|---|---|---|---|
| | 20528 C.n. | 21538 C.a. | 21500 C.g. | 21321 C.k. | 20521 C.t. | 20517 C.k. |
| 7a | ≧50 | ≧50 | ≧50 | ≧50 | ≧50 | ≧50 |
| 7b | 6.25 | ≧50 | ≧50 | ≧50 | ≧50 | ≧50 |
| 7c | ≧50 | ≧50 | ≧50 | ≧50 | ≧50 | 0.39 |
| 7d | 12.5 | ≧50 | ≧50 | ≧50 | ≧50 | 0.39 |
| 7e | ≧50 | ≧50 | ≧50 | ≧50 | ≧50 | ≧50 |
| 8a | ≧50 | ≧50 | ≧50 | ≧50 | ≧50 | ≧50 |
| 8b | ≧50 | ≧50 | ≧50 | ≧50 | ≧50 | ≧50 |
| 8c | ≧50 | ≧50 | ≧50 | ≧50 | ≧50 | ≧50 |
| 8d | ≧50 | ≧50 | ≧50 | ≧50 | ≧50 | ≧50 |
| 8e | ≧50 | ≧50 | ≧50 | ≧50 | ≧50 | ≧50 |

TABLE 2

The In vitro Susceptibility Testing of Imidazole Antifungals agains yeasts

| CCRC# Strain | MIC (ug/ml) | | | | | |
|---|---|---|---|---|---|---|
| | 20528 C.n. | 21538 C.a. | 21500 C.g. | 21321 C.k. | 20521 C.t. | 20517 C.k. |
| 9a | ≧50 | ≧50 | ≧50 | ≧50 | ≧50 | ≧50 |
| 9b | 0.391 | ≧50 | ≧50 | ≧50 | ≧50 | ≦0.098 |
| 9c | ≧50 | ≧50 | ≧50 | ≧50 | ≧50 | 0.39 |
| 9d | 1.563 | ≧50 | ≧50 | ≧50 | ≧50 | 0.195 |
| 9e | ≧50 | ≧50 | ≧50 | ≧50 | ≧50 | ≧50 |
| 11a | ≧50 | ≧50 | ≧50 | ≧50 | ≧50 | 6.25 |
| 11b | 3.125 | ≧50 | ≧50 | ≧50 | ≧50 | 3.125 |
| 11c | ≧50 | ≧50 | ≧50 | ≧50 | ≧50 | ≧50 |
| 11d | 3.125 | ≧50 | ≧50 | ≧50 | ≧50 | ≧50 |
| 11e | ≧50 | ≧50 | ≧50 | ≧50 | ≧50 | 6.25 |

Test Yeast Strain:
1. CCRC 20528 Cryptococcus neoformans
2. CCRC 21538 Candida albicans
3. CCRC 21500 Candida guilliermondii
4. CCRC 21321 Candida krusei
5. CCRC 20521 Candida tropicalis
6. CCRC 20517 Candida kefyr

TABLE 3

The In vitro Susceptibility Testing of Triazole Antifungals agains molds

| CCRC # Strain[b] | MIC (ug/ml)[a] | | | |
|---|---|---|---|---|
| | 32066 T.m. | 32121 F.o. | 30502 A.f. | 30006 A.f. |
| 7a | 4 | ≧50 | ≧50 | ≧50 |
| 7b | 0.25 | ≧50 | 4 | 25 |
| 7c | 1 | ≧50 | ≧50 | ≧50 |
| 7d | 4 | ≧50 | ≧50 | ≧50 |
| 7e | 2 | ≧50 | ≧50 | ≧50 |
| 8a | ≧50 | ≧50 | ≧50 | ≧50 |
| 8b | 25 | ≧50 | ≧50 | ≧50 |
| 8c | ≧50 | ≧50 | ≧50 | ≧50 |

TABLE 3-continued

The In vitro Susceptibility Testing of Triazole Antifungals agains molds

| | MIC (ug/ml)[a] | | | |
|---|---|---|---|---|
| CCRC # | 32066 | 32121 | 30502 | 30006 |
| Strain[b] | T.m. | F.o. | A.f. | A.f. |
| 8d | ≧50 | ≧50 | ≧50 | ≧50 |
| 8e | ≧50 | ≧50 | ≧50 | ≧50 |

[a]MIC: Minimumal Inhibition Concentration (ug/ml)
[b]Mold Strains:
CCRC32066: *Trichophyton mentagrophytes*
CCRC32121: *Fusarium oxysporum*
CCRC30502: *Aspergillus fumigatus*
CCRC30006: *Aspergillus flavus*

TABLE 4

The In vitro Susceptibility Testing of Imidazole Antifungals agains molds

| | MIC (ug/ml)[a] | | | |
|---|---|---|---|---|
| CCRC # | 32066 | 32121 | 30502 | 30006 |
| Strain[b] | T.m. | F.o. | A.f. | A.f. |
| 9a | 0.195 | ≧50 | 25 | 25 |
| 9b | 0.195 | ≧50 | 3.125 | 0.195 |
| 9c | 0.098 | ≧50 | 12.5 | 6.25 |
| 9d | 6.25 | 12.5 | 0.391 | 0.781 |
| 9e | 0.391 | ≧50 | 6.25 | 0.781 |
| 11a | ≧50 | ≧50 | ≧50 | ≧50 |
| 11b | ≧50 | ≧50 | ≧50 | ≧50 |
| 11c | ≧50 | ≧50 | ≧50 | ≧50 |
| 11d | 5 | ≧50 | ≧50 | ≧50 |
| 11e | 2 | ≧50 | ≧50 | ≧50 |

[a]MIC: Minimumal Inhibition Concentration (ug/ml)
[b]Mold Strains:
CCRC32066: *Trichophyton mentagrophytes*
CCRC32121: *Fusarium oxysporum*
CCRC30502: *Aspergillus fumigatus*
CCRC30006: *Aspergillus flavus*

We claim:

1. A compound of formula (I)

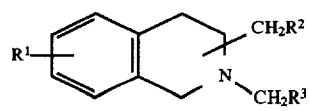

wherein

R$^1$ is an optional substitution at any position of the phenyl ring and is selected from halogen, —NO$_2$, —NH$_2$, —OH, —O—C$_{1-6}$alkyl;

—CH$_2$R$^2$ is a substitution at the 1- or 3- position of 1,2,3,4-tetrahydroisoquinoline, wherein R$^2$ is an azole group selecting from the group consisting of pyrrole, pyrazole, carbazole, benzimidazole, imidazole and triazole; and R$^3$ is phenyl optionally substituted with one or more halogen;

and pharmaceutical salts thereof.

2. A compound of claim 1, wherein R$^2$ is a triazolyl, imidazolyl or benzimidazolyl group.

3. A compound of claim 1 which is selected from the group consisting of:

2-Phenylmethyl-1-(1H-1,2,4-triazole-1-yl)methyl-1,2,3,4-tetrahydroisoquinoline;

2-(4-Chlorophenyl)methyl-1-(1H-1,2,4-triazole-1-yl)methyl-1,2,3,4-tetrahydroisoquinoline;

2-(4-Fluorophenyl)methyl-1-(1H-1,2,4-triazole-1-yl)methyl-1,2,3,4-tetrahydroisoquinoline;

2-(2,4-Dichlorophenyl)methyl-1-(1H-1,2,4-triazole-1-yl)methyl-1,2,3,4-tetrahydroisoquinoline;

2-(2,4-Difluorophenyl)methyl-1-(1H-1,2,4-triazole-1-yl)methyl-1,2,3,4-tetrahydroisoquinoline;

(S)-2-Phenylmethyl-3-(1H-1,2,4-triazole-1-yl)methyl-1,2,3,4-tetrahydroisoquinoline;

(S)-2-(4-Chlorophenyl)methyl-3-(1H-1,2,4-triazole-1-yl)methyl-1,2,3,4-tetrahydroisoquinoline;

(S)-2-(4-Fluorophenyl)methyl-3-(1H-1,2,4-triazole-1-yl)methyl-1,2,3,4-tetrahydroisoquinoline;

(S)-2-(2,4-Dichlorophenyl)methyl-3-(1H-1,2,4-triazole-1-yl)methyl-1,2,3,4-tetrahydroisoquinoline;

(S)-2-(2,4-Difluorophenyl)methyl-3-(1H-1,2,4-triazole-1-yl)methyl-1,2,3,4-tetrahydroisoquinoline;

2-Phenylmethyl-1-(1H-1,3-imidazole-1-yl)methyl-1,2,3,4-tetrahydroisoquinoline;

2-(4-Chlorophenyl)methyl-1-(1H-1,3-imidazole-1-yl)methyl-1,2,3,4-tetrahydroisoquinoline;

2-(4-Fluorophenyl)methyl-1-(1H-1,3-imidazole-1-yl)methyl-1,2,3,4-tetrahydroisoquinoline;

2-(2,4-Dichlorophenyl)methyl-1-(1H-1,3-imidazole-1-yl)methyl-1,2,3,4-tetrahydroisoquinoline;

2-(2,4-Difluorophenyl)methyl-1-(1H-1,3-imidazole-1-yl)methyl-1,2,3,4-tetrahydro-isoquinoline;

(S)-2-Phenylmethyl-3-(1H-1,3-imidazole-1-yl)methyl-1,2,3,4-tetrahydroisoquinoline;

(S)-2-(2-Chlorophenyl)methyl-3-(1H-1,3-imidazole-1-yl)methyl-1,2,3,4-tetrahydroisoquinoline;

(S)-2-(2-Fluorophenyl)methyl-3-(1H-1,3-imidazole-1-yl)methyl-1,2,3,4-tetrahydroisoquinoline;

(S)-2-(2,4-Dichlorophenyl)methyl-3-(1H-1,3-imidazole-1-yl)methyl-1,2,3,4-tetrahydroisoquinoline;

(S)-2-(2,4-Difluorophenyl)methyl-3-(1H-1,3-imidazole-1-yl)methyl-1,2,3,4-tetrahydro-isoquinoline;

2-Phenylmethyl-1-(1H-1,3-benzimidazole-1-yl)methyl-1,2,3,4-tetrahydroisoquinoline;

2-(4-Chlorophenyl)methyl-1-(1H-1,3-benzimidazole-1-yl)methyl-1,2,3,4-tetrahydroisoquinoline;

2-(4-Fluorophenyl)methyl-1-(1H-1,3-benzimidazole-1-yl)methyl-1,2,3,4-tetrahydro-isoquinoline;

2-(2,4-Dichlorophenyl)methyl-1-(1H-1,3-benzimidazole-1-yl)methyl-1,2,3,4-tetrahydro-isoquinoline;

2-(2,4-Difluorophenyl)methyl-1-(1H-1,3-benzimidazole-1-yl)methyl-1,2,3,4-tetrahydro-isoquinoline;

(S)-2-Phenylmethyl-3-(1H-1,3-benzimidazole-1-yl)methyl-1,2,3,4-tetrahydroisoquinoline;

(S)-2-(4-Chlorophenyl)methyl-3-(1H-1,3-benzimidazole-1-yl)methyl-1,2,3,4-tetrahydroisoquinoline;

(S)-2-(4-Fluorophenyl)methyl-3-(1H-1,3-benzimidazole-1-yl)methyl-1,2,3,4-tetrahydro-isoquinoline;

(S)-2-(2,4-Dichlorophenyl)methyl-3-(1H-1,3-benzimidazole-1-yl)methyl-1,2,3,4-tetrahydroisoquinoline;

(S)-2-(2,4-Difluorophenyl)methyl-3-(1H-1,3-benzimidazole-1-yl)methyl-1,2,3,4-tetrahydroisoquinoline;

2-Phenylcarbonyl-1-(1H-1,2,4-triazole-1-yl)methyl-1,2,3,4-tetrahydroisoquinoline;

2-(4-Chlorophenyl)carbonyl-1-(1H-1,2,4-triazole-1-yl)methyl-1,2,3,4-tetrahydroisoquinoline;

2-(4-Fluorophenyl)carbonyl-1-(1H-1,2,4-triazole-1-yl)methyl-1,2,3,4-tetrahydroisoquinoline;

2-(2,4-Dichlorophenyl)carbonyl-1-(1H-1,2,4-triazole-1-yl)methyl-1,2,3,4-tetrahydroisoquinoline;

2-(2,4-Difluorophenyl)carbonyl-1-(1H-1,2,4-triazole-1-yl)methyl-1,2,3,4-tetrahydroisoquinoline;

(S)-2-Phenylcarbonyl-3-(1H-1,2,4-triazole-1-yl)methyl-1,2,
3,4-tetrahydroisoquinoline;
(S)-2-(4-Chlorophenyl)carbonyl-3-(1H-1,2,4-triazole-1-yl)
methyl-1,2,3,4-tetrahydroisoquinoline;
(S)-2-(4-Fluorophenyl)carbonyl-3-(1H-1,2,4-triazole-1-yl)
methyl-1,2,3,4-tetrahydroisoquinoline;
(S)-2-(2,4-Dichlorophenyl)carbonyl-3-(1H-1,2,4-triazole-1-
yl)methyl-1,2,3,4-tetrahydroisoquinoline;
(S)-2-(2,4-Difluorophenyl)carbonyl-3-(1H-1,2,4-triazole-1-
yl)methyl-1,2,3,4-tetrahydroisoquinoline;
2-Phenylcarbonyl-1-(1H-1,3-imidazole-1-yl)methyl-1,2,3,
4-tetrahydroisoquinoline;
2-(4-Chlorophenyl)carbonyl-1-(1H-1,3-imidazole-1-yl)
methyl-1,2,3,4-tetrahydroisoquinoline;
2-(4-Fluorophenyl)carbonyl-1-(1H-1,3-imidazole-1-yl)
methyl-1,2,3,4-tetrahydroisoquinoline;
2-(2,4-Dichlorophenyl)carbonyl-1-(1H-1,3-imidazole-1-yl)
methyl-1,2,3,4-tetrahydroisoquinoline;
2-(2,4-Difluorophenyl)carbonyl-1-(1H-1,3-imidazole-1-yl)
methyl-1,2,3,4-tetrahydroisoquinoline;
(S)-2-Phenylcarbonyl-3-(1H-1,3-imidazole-1-yl)methyl-1,
2,3,4-tetrahydroisoquinoline;
(S)-2-(4-Chlorophenyl)carbonyl-3-(1H-1,3-imidazole-1-yl)
methyl-1,2,3,4-tetrahydroisoquinoline;
(S)-2-(4-Fluorophenyl)carbonyl-3-(1H-1,3-imidazole-1-yl)
methyl-1,2,3,4-tetrahydroisoquinoline;
(S)-2-(2,4-Dichlorophenyl)carbonyl-3-(1H-1,3-imidazole-
1-yl)methyl-1,2,3,4-tetrahydroisoquinoline;
(S)-2-(2,4-Difluorophenyl)carbonyl-3-(1H-1,3-imidazole-
1-yl)methyl-1,2,3,4-tetrahydro-isoquinoline;
2-Phenylcarbonyl-1-(1H-1,3-benzimidazole-1-yl)methyl-1,
2,3,4-tetrahydroisoquinoline;
2-(4-Chlorophenyl)carbonyl-1-(1H-1,3-benzimidazole-1-
yl)methyl-1,2,3,4-tetrahydroisoquinoline;
2-(4-Fluorophenyl)carbonyl-1-(1H-1,3-benzimidazole-1-yl)
methyl-1,2,3,4-tetrahydroisoquinoline;
2-(2,4-Dichlorophenyl)carbonyl-1-(1H-1,3-benzimidazole-
1-yl)methyl-1,2,3,4-tetrahydro-isoquinoline;
2-(2,4-Difluorophenyl)carbonyl-1-(1H-1,3-benzimidazole-
1-1)methyl-1,2,3,4-tetrahydro-isoquinoline;
(S)-2-Phenylcarbonyl-3-(1H-1,3-benzimidazole-1-yl)
methyl-1,2,3,4-tetrahydroisoquinoline;
(S)-2-(4-Chlorophenyl)carbonyl-3-(1H-1,3-benzimidazole-
1-yl)methyl-1,2,3,4-tetrahydroisoquinoline;
(S)-2-(4-Fluorophenyl)carbonyl-3-(1H-1,3-benzimidazole-
1-yl)methyl-1,2,3,4-tetrahydro-isoquinoline;
(S)-2-(2,4-Dichlorophenyl)carbonyl-3-(1H-1,3-
benzimidazole-1-yl)methyl-1,2,3,4-
tetrahydroisoquinoline; and
(S)-2-(2,4-Difluorophenyl)carbonyl-3-(1H-1,3-
benzimidazole-1-yl)methyl-1,2,3,4-
tetrahydroisoquinoline.

4. A compound of claim 3 which is selected from the group consisting of:

2-Phenylmethyl-1-(1H-1,2,4-triazole-1-yl)methyl-1,2,3,4-
tetrahydroisoquinoline;
2-(4-Chlorophenyl)methyl-1-(1H-1,2,4-triazole-1-yl)
methyl-1,2,3,4-tetrahydroisoquinoline;
2-(4-Fluorophenyl)methyl-1-(1H-1,2,4-triazole-1-yl)
methyl-1,2,3,4-tetrahydroisoquinoline;
2-(2,4-Dichlorophenyl)methyl-1-(1H-1,2,4-triazole-1-yl)
methyl-1,2,3,4-tetrahydroisoquinoline;
2-(2,4-Difluorophenyl)methyl-1-(1H-1,2,4-triazole-1-yl)
methyl-1,2,3,4-tetrahydroisoquinoline;
(S)-2-Phenylmethyl-3-(1H-1,2,4-triazole-1-yl)methyl-1,2,3,
4-tetrahydroisoquinoline;
(S)-2-(4-Chlorophenyl)methyl-3-(1H-1,2,4-triazole-1-yl)
methyl-1,2,3,4-tetrahydroisoquinoline;
(S)-2-(4-Fluorophenyl)methyl-3-(1H-1,2,4-triazole-1-yl)
methyl-1,2,3,4-tetrahydroisoquinoline;
(S)-2-(2,4-Dichlorophenyl)methyl-3-(1H-1,2,4-triazole-1-
yl)methyl-1,2,3,4-tetrahydroisoquinoline;
(S)-2-(2,4-Difluorophenyl)methyl-3-(1H-1,2,4-triazole-1-
yl)methyl-1,2,3,4-tetrahydroisoquinoline;
2-Phenylmethyl-1-(1H-1,3-imidazole-1-yl)methyl-1,2,3,4-
tetrahydroisoquinoline;
2-(4-Chlorophenyl)methyl-1-(1H-1,3-imidazole-1-yl)
methyl-1,2,3,4-tetrahydroisoquinoline;
2-(4-Fluorophenyl)methyl-1-(1H-1,3-imidazole-1-yl)
methyl-1,2,3,4-tetrahydroisoquinoline;
2-(2,4-Dichlorophenyl)methyl-1-(1H-1,3-imidazole-1-yl)
methyl-1,2,3,4-tetrahydroisoquinoline;
2-(2,4-Difluorophenyl)methyl-1-(1H-1,3-imidazole-1-yl)
methyl-1,2,3,4-tetrahydro-isoquinoline;
(S)-2-Phenylmethyl-3-(1H-1,3-imidazole-1-yl)methyl-1,2,
3,4-tetrahydroisoquinoline;
(S)-2-(4-Chlorophenyl)methyl-3-(1H-1,3-imidazole-1-yl)
methyl-1,2,3,4-tetrahydroisoquinoline;
(S)-2-(4-Fluorophenyl)methyl-3-(1H-1,3-imidazole-1-yl)
methyl-1,2,3,4-tetrahydroisoquinoline;
(S)-2-(2,4-Dichlorophenyl)methyl-3-(1H-1,3-imidazole-1-
yl)methyl-1,2,3,4-tetrahydroisoquinoline;
(S)-2-(2,4-Difluorophenyl)methyl-3-(1H-1,3-imidazole-1-
yl)methyl-1,2,3,4-tetrahydro-isoquinoline;
2-Phenylmethyl-1-(1H-1,3-benzimidazole-1-yl)methyl-1,2,
3,4-tetrahydroisoquinoline;
2-(4-Chlorophenyl)methyl-1-(1H-1,3-benzimidazole-1-yl)
methyl-1,2,3,4-tetrahydroisoquinoline;
2-(4-Fluorophenyl)methyl-1-(1H-1,3-benzimidazole-1-yl)
methyl-1,2,3,4-tetrahydro-isoquinoline;
2-(2,4-Dichlorophenyl)methyl-1-(1H-1,3-benzimidazole-1-
yl)methyl-1,2,3,4-tetrahydro-isoquinoline;
2-(2,4-Difluorophenyl)methyl-1-(1H-1,3-benzimidazole-1-
yl)methyl-1,2,3,4-tetrahydro-isoquinoline.

5. The compound of claim 3 which is 2-(4-Chlorophenyl)methyl-1-(1H-1,2,4-triazole-1-yl)methyl-1,2,3,4-tetrahydroisoquinoline.

6. The compound of claim 3 which is 2-(4-Chlorophenyl)methyl-1-(1H-1,3-imidazole-1-yl)methyl-1,2,3,4-tetrahydroisoquinoline.

7. The compound of claim 3 which is 2-(2,4-Dichlorophenyl)methyl-1-(1H-1,3-imidazole-1-yl)methyl-1,2,3,4-tetrahydroisoquinoline.

8. A pharmaceutical composition for inhibiting fungal growth which comprises an effective fungal inhibitory amount of the compound of claim 1 in a pharmaceutically acceptable carrier.

9. A pharmaceutical composition for inhibiting fungal growth which comprises an effective fungal inhibitory amount of the compound of claim 3 in a pharmaceutically acceptable carrier.

10. A method of inhibiting fungal growth which comprises administrating an effective fungal inhibitory amount of the compound of claim 1.

11. A method of inhibiting fungal growth which comprises administrating an effective fungal inhibitory amount of the compound of claim 3.

* * * * *